United States Patent [19]

Raspanti

[11] Patent Number: 5,801,244
[45] Date of Patent: Sep. 1, 1998

[54] SUNSCREENS

[75] Inventor: Giuseppe Raspanti, Bergamo, Italy

[73] Assignee: 3V Inc., Weehawken, N.J.

[21] Appl. No.: 620,953

[22] Filed: Mar. 25, 1996

[51] Int. Cl.⁶ .................................................. C07D 251/70
[52] U.S. Cl. .................................................. 544/197
[58] Field of Search .................................................. 544/197

[56] References Cited

U.S. PATENT DOCUMENTS

| 2,328,961 | 9/1943 | D'Alelio et al. | 544/197 |
| 3,697,520 | 10/1972 | Winter | 544/197 |
| 5,233,040 | 8/1993 | Raspanti | 544/197 |

FOREIGN PATENT DOCUMENTS

| 517104 | 2/1992 | European Pat. Off. | 544/197 |
| 570838 | 11/1993 | European Pat. Off. | 544/197 |

*Primary Examiner*—John M. Ford
*Attorney, Agent, or Firm*—Griffin, Butler Whisenhunt & Szipl, LLP

[57] ABSTRACT

Compounds of formula

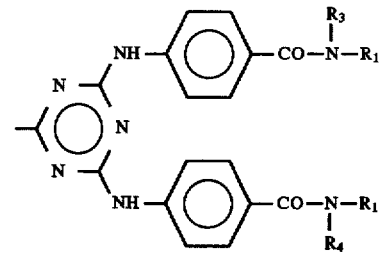

(I)

wherein R and $R_1$ can be the same or different and are $C_1$–$C_{18}$ straight or branched alkyl, $C_5$–$C_{12}$ cycloalkyl, optionally substituted with one or more $C_1$–$C_4$ alkyl; $R_2$, $R_3$ and $R_4$ can be the same or different and have the same meaning of R or are hydrogen.

Said compounds are useful as photostabilizing agents for synthetic polymers and as sunscreens for the protection of human skin from sunburns.

When used as photostabilizing agents or sunscreens, the above described compounds are more resistant to hydrolysis.

3 Claims, No Drawings

SUNSCREENS

The present invention relates to photostabilization of synthetic polymers and the protection of human skin from sunlight radiations.

BACKGROUND OF THE INVENTION

It is known that due to the action of sunlight radiations ranging from 280 to 400 nm the organic materials, such as for example plastics and varnishes, are more or less quickly destroyed; a destruction which reveals in the form of yellowing, discoloration, brittlening and generally as loss of mechanical properties of the organic material.

It is also known that UV radiations are noxious to human skin; in particular radiations having wavelength between 290 and 320 nm, so-called UV-B radiations, which cause erythema and sunburns, whose severity depends on the length of exposition.

Derivatives of 1,3,5-triazine were proposed as sunscreens in patents DE 3 206 398, U.S. Pat. No. 5,233,040 and U.S. Pat. No. 5,346,691, but the results coming from their use is not yet completely satisfactory. In fact, the compounds described in the above patents, contain in their chemical structure one or two ester groups and undergo to a more or less high degree of hydrolysis depending on the composition or the pH of the cosmetic formulation to which they are added, on the temperature and time of storage of the formulation itself.

Hydrolysis can cause unwanted alterations of the cosmetic formulation, such as for example pH and/or color variations, destabilization of the formulation with formation of precipitates and/or coagulates and subsequent loss of activity and impossibility of use.

It is still presently felt the need for the availability of sunscreens which are resistant to hydrolysis also in conditions of long conservation in wide intervals of temperature, as it can happen in cosmetic formulations kept at home.

At the same time, it is desirable to have photostabilizing agents for synthetic polymers which are stable at conditions of use.

Moreover, the sunscreens, or the photostabilizing agents must have high absorption on a wide wavelength band.

DISCLOSURE OF THE INVENTION

It has now surprisingly been found that aniline derivatives of symmetric triazines not only have high absorption capacity for the ultraviolet radiations but also are highly resistant to hydrolysis.

It is an object of the present invention a compound of formula (I)

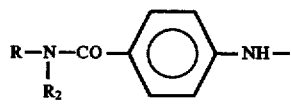

(I)

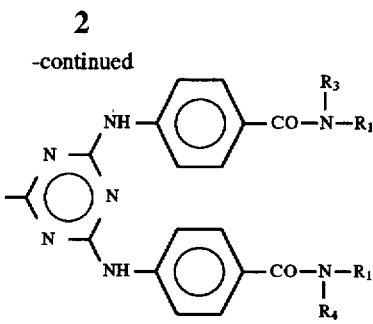

wherein R and $R_1$ can be the same or different and are $C_1$–$C_{18}$ straight or branched alkyl, $C_5$–$C_{12}$ cycloalkyl optionally substituted with one or more $C_1$–$C_4$ alkyl; $R_2$, $R_3$ and $R_4$ can be the same or different and have the same meaning of R or are hydrogen.

The compounds of formula (I) are useful as photostabilizing agents for synthetic polymers, these compounds are also useful as sunscreens for the protection of human skin from sunlight.

It is a further object of the present invention a process for the preparation of the compounds of formula (I).

It is another object of the present invention a dermatological and cosmetic composition containing one or more compounds of formula (I) as sunscreens. These and other objects of the present invention will subsequently be described in detail also by means of examples.

DETAILED DISCLOSURE OF THE INVENTION

In the compound of formula (I), examples of $C_1$–$C_{18}$ alkyl comprise methyl, ethyl, isopropyl, t-butyl, n-hexyl, 2-ethylbutyl, 2-ethylhexyl, 1,1,3,3-tetramethylbutyl, dodecyl, hexadecyl, octadecyl.

Examples of optionally substituted cycloalkyl are cyclohexyl, cyclopentyl, 2-, 3-, or 4-methylcyclohexyl, ter-butylcyclohexyl.

A first group of preferred compounds are those wherein R and $R_1$ have the above defined meaning, $R_2$ is hydrogen, $R_3$ and $R_4$ have the same meaning of R and $R_1$, or are hydrogen.

A second group of preferred compounds are those wherein $R_2$, $R_3$, $R_4$ are hydrogen, R and $R_1$ have the above defined meaning.

The compounds according to the present invention absorb UV radiations in a particularly intense way in the range from 290 to 320 nm. They can be then effectively used as sunscreens for the protection of synthetic polymers, of varnishes and especially in cosmetic industry for the preparation of cosmetic compositions with high Sun Protecting Factor (SPF) intended for protection of human skin from sunlight radiations.

The synthesis of the compounds of formula (I) is carried out preferably by reacting a compound of formula (II)

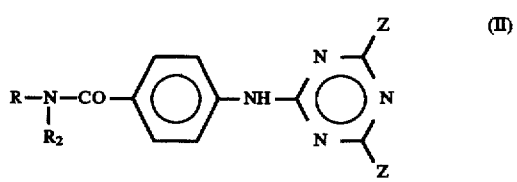

(II)

with p-aminobenzamides of formula (III) and subsequently, in case when $R_4$ is different from $R_3$, with p-aminobenzamides of formula (IIIa)

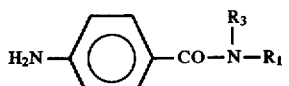

(III)

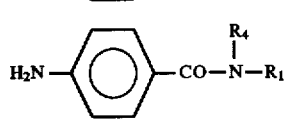

(IIIa)

or reacting a compound of formula (IV)

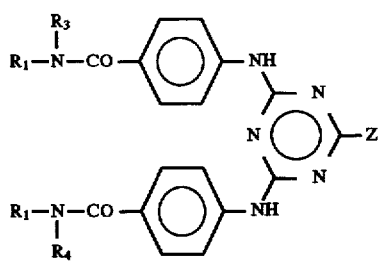

(IV)

with p-aminobenzamides of formula (V)

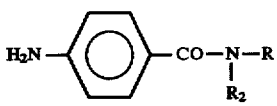

(V)

where R, $R_1$, $R_2$, $R_3$ and $R_4$ have the above defined meanings, Z is bromine or preferably chlorine.

The intermediates of formula (II) and (IV) are prepared according to well known processes from tribromotriazine, or preferably from trichlorotriazine and aminobenzamides of formula (V) or respectively of formula (III), for example as described in Chem. Abstr. 50, 13101 b (1956); Chem. Abstr. 54, 20061 h (1960); Chem. Abstr. 70, 37844 (1969); J. Am. Chem. Soc. 73, 2981 (1951).

The reaction is carried out at a temperature from 50° to 200° C. in suitable organic solvents, such as for example acetonitrile, ketones as acetone, methylethyl ketone; ether as diethyl ether, diisopropyl ether, tetrahydrofuran, dioxane, aliphatic or aromatic hydrocarbons, as pentane, eptane, octane, cyclohexane, benzene, toluene, xylene or their mixtures; esters as ethyl acetate. The reaction can optionally be carried out in the presence of acid acceptor, such as for example alkali or alkaline-earth hydroxides, alkali metal carbonate or bicarbonates.

The intermediates of formula (II) and (IV) can be recovered and purified before the subsequent reaction with the compounds of formula (V) and (III), alternatively, it is possible directly to prosecute further, without isolating or purifying the intermediate.

The reaction of the trichlorotriazine to substitute the three chlorine atoms with amino residues, which can be the same or different are well known and widely described in the chemical literature, particularly for the preparation of some classes of dyes, for example as described in Chem. Abstr. 55, 8864 h (1961); Chem. Abstr. 61, 3233 d (1964); Chem. Abstr. 65, 15545 g (1966) and optical brighteners, for example as described in Chem. Abstr. 48, 10773 h (1954); Chem. Abstr. 78, 112679 (1973); Chem. Abstr. 81, 93087 (1974).

p-Aminobenzamides of formula (III) and (V) can be prepared, according to well known methods, for example similarly to the method disclosed in DE 2 327 506 from p-nitrobenzoyl chloride and the corresponding amine and subsequent reduction of the p-nitro-benzamides.

Cosmetic compositions according to the present invention, containing at least a compound of formula (I), are useful for the treatment of human skin, of hairs or make-up, in decorative cosmetic, also for the protection of human skin from sunlight.

The compositions may be of different types, for example solutions, lotions, water-in-oil or oil-in-water emulsions; or also in the form of gel, lipstick, aerosol.

The compositions are prepared by formulating conventional ingredients, such as for example oils, fats, emollients, hydrating agents, moisturizing agents, softening agents, preservatives, surfactants, thickening agents, antifoam, perfumes, pigments, dyes and other else such as alcohols, polyols, electrolytes, silicone derivatives. The most commonly used solvents are triglycerides of caprinic or caprilic acid, for example castor oil, esters of fatty acids with isopropanol, propylene glycol, glycerin, propylene glycol-monomethyl or monoethyl or monobutyl ether.

The present invention also comprises a method for protecting cosmetics from UV radiation by adding a sufficient amount of the compounds of formula (I), in this case it is the composition whose ingredients can undergo indesiderate degradation or coloring due to light to be protected from radiation induced-degradation. Such a composition may be for example hair shampoos and lacquers, hairdress lotions, hair-dye compositions, formulations for make-up, such as nail lacquers, foundation, lipstick. Preferred cosmetic compositions are those for the protection of human skin from sun radiations. A skilled person shall be able to determine the sufficient amount of compound of formula (I) to add to a cosmetic composition in order to protect it from photodegradation.

For the purpose of protecting human skin from sunburns, the cosmetic compositions according to the present invention can contain one or more compounds of formula (I), in an amount comprised from 0.1 to 20%, preferably from 0.5 to 15% by weight with respect to the total weight of the composition. Other than compounds of formula (I), the claimed compositions can contain in combination also other sunscreens and particularly those having a maximum absorption comprised from 320 to 400 nm.

Well known sunscreens, which can be combined with the compounds of formula (I) are for example: 3-(4-methylbenzylydene)-camphor; 2-ethylhexyl-(4-dimethylamino) benzoate, 2-ethylhexyl-4-methoxy-cinnamate, menthyl salicilate, 2-hydroxy-4-methoxy-benzophenone, 2,4,6-trianilino-(p-carbo-2-ethylhexyloxy)-1,3,5-triazine, 4-(1,1-dimethylethyl)-4-methoxydibenzoyl methane, salts of 2-phenyl-benzimidazol-5-sulfonic acid or of 2-hydroxy-4-methoxy-benzophenone-5-sulfonic acid.

The cosmetic compositions according to the present invention may contain also inorganic pigments, commonly used in cosmetics, such as for example those used for the protection of human skin from UV radiations, for example titanium, zinc, silicon or aluminium oxides.

According to the present invention as a polymeric material, which can be protected from UV radiation, it is intended polyethylene, polypropylene, polystyrene, polybutadiene, polyisoprene and their copolymers, polyvinyl acetate and its copolymers, particularly with polyethylene, polyesters such as polyethylenterephthalate, polyamides such as Nylon 6 and Nylon 6,6, polyurethanes, polyacrilates, polymethacrylates, polyvinyl chloride.

The compounds of formula (I) can be incorporated in polymers to be stabilized by means of any known method for mixing or blending additives to polymeric materials; for example, they can be mixed with the polymer in a suitable blender or mixer, or added in the form of solution or suspension in a suitable solvent such as methanol, ethanol, acetone, chloroform, then removing the solvent after mixing with the polymer, which can be in the form of powder, granulate or suspension or finally can be added to the polymer during the preparation of the same, for example in the last step of preparation.

The compounds of formula (I) can be used also in combination with other stabilizing agents and additives generally used for polymers, such as for example phenol-based antioxydants, phosphites, hindered amines and particularly those containing in their structure the 2,2,6,6-tetramethylpiperidine group, other types of UV-Absorber based on benzotriazoles or benzophenones, plastifiers, lubricants, antistatic agents, flame retardants, titanium oxide.

The amount of compounds of formula (I) necessary to an effective stabilization of the polymer depends on different factors, such as the kind and the characteristics of the polymer, the use to which it is intended, the intensity of the radiation, the duration of exposure and the presence, if any, of other stabilizing agents.

Generally, an amount comprised from 0.01 to 5% by weight of the polymer, preferably from 0.05 to 2% is sufficient, but it is understood that a skilled technician in the field shall be able to find a suitable amount.

The following examples further illustrate the invention.

EXAMPLE 1

19.8 g of 4-amino-ter-octyl-benzamide were added to 4.6 g of 1,3,5-trichlorotriazine dissolved in 150 ml of xylene. The reaction mixture was slowly heated to reflux and stirred for 5 hours.

The precipitate formed after cooling, was filtered and recrystallized from toluene.

The compound of formula VI was obtained as whitish solid with M.p. 158°–160° C. and $E_r^1$: of 1324 at 302 nm.

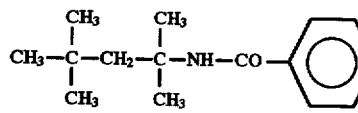
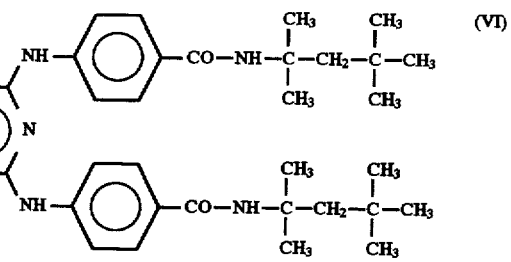

(VI)

EXAMPLE 2

15.6 g of 4-amino-2-ethylhexylbenzamide were added to 11.8 g of 2,4-dichloro-6-[4-(ter-octylbenzamide)amino]-1,3,5-s-triazine dissolved in 150 ml of xylene.

The mixture was warmed to reflux and stirred for 6 hours.

The solvent was distilled off and the residue recrystallized from a mixture of toluene and octane.

The compound of formula (VII) was obtained as a whitish substance with M.p. 137°–140° C. $E_r^1$: 1279 at 302 nm.

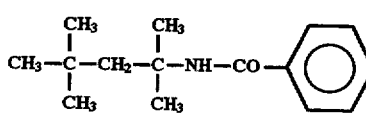
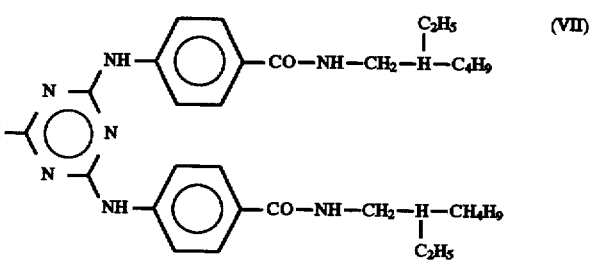

(VII)

Following the procedure as described in the examples 1 or 2 the compounds of formula (Ia) listed in Table 1 were obtained.

TABLE 1

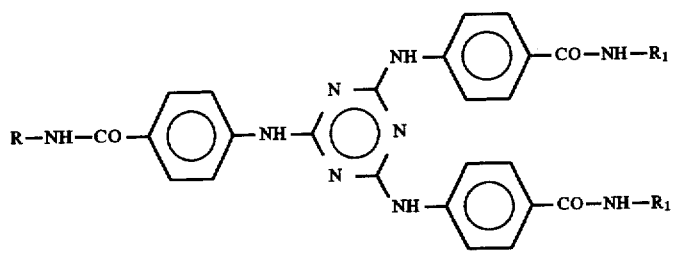

(Ia)

| Example | R | $R_1$ | M.p. °C. | $E_1^1$: | nm |
|---|---|---|---|---|---|
| 3 | $(CH_3)_3C$ | $(CH_3)_3C$ | >250° | 1466 | 302 |
| 4 | ter-$C_8H_{17}$ | $(CH_3)_3C$ | 171–174 | 1478 | 302 |
| 5 | $C_4H_9$—CH—$CH_2$<br>       \|<br>       $C_2H_5$ | $(CH_3)_3C$ | 236–239 | 1547 | 302 |

EXAMPLE 6

Sun Cream

| | |
|---|---|
| Polyglycole (Arlacel 165 ICI) | 2.0 g |
| Glycerine monostearate | 4.0 g |
| Benzoate of $C_{12}$-$C_{15}$ alcole | 5.0 g |
| Cetylstearyl alcohol | 3.0 g |
| Miristic alcohol with 3 moles of propylene oxide (Witcamol APM-Witco) | 29.0 g |
| Compound of Example 1 | 3.0 g |
| Perfume | 0.3 g |
| Distilled water q.s. | 100 g |

The fatty phase was warmed to 80°–90° C., the compound of Example 1 was added, then the mixture was added to water, containing the hydrosoluble compounds, heated to 80°–90° C. Warm-stirring was continued for 15–20 minutes.

After slow cooling perfume was added.

EXAMPLE 7

Sun-milk

| | |
|---|---|
| Fatty acid Triglycerides | 20.0 g |
| Cetylstearyl alcohol | 2.0 g |
| Lanoline | 4.0 g |
| Cetyl alcohol | 2.0 g |
| Silicone oil | 0.4 g |
| Compound of Example 3 | 2.0 g |
| Abiol (preservative by 3V-Sigma) | 0.2 g |
| Synthalen M (thickening agent by 3V-Sigma) | 0.1 g |
| Triethanol amine | 0.15 g |
| Perfume | 0.3 g |
| Distilled water q.s. | 100 g |

The preparation was carried out as in Example 7.

EXAMPLE 8

Day-cream

| | |
|---|---|
| $C_8$-$C_{12}$ acid triglycerides | 29.0 g |
| Glycerol monostearate | 7.0 g |
| Stearic Acid | 2.0 g |
| Lanoline | 4.0 g |

-continued

| | |
|---|---|
| Preservative | 0.2 g |
| Compound of Example 4 | 1.0 g |
| 4-(dimethylethyl)-4'-methoxydibenzoyl-methane (Parsol 1789-Givaudan) | 1.0 g |
| Propylene glycole | 2.5 g |
| Triethanolamine | 0.5 g |
| Perfume | 0.3 g |
| Distilled water q.s. | 100 g |

The composition was prepared as described in Example 6.

EXAMPLE 9

Alcoholic Gel

| | |
|---|---|
| Propylene glycol | 25.0 g |
| Ethyl alcohol | 25.0 g |
| Synthalen M (thickening agent by 3V-Sigma) | 0.6 g |
| Compound of Example 1 | 2.5 g |
| Triethanolamine | 0.3 g |
| Preservative | 0.3 g |
| Perfume | 0.3 g |
| Distilled water q.s. | 100 g |

Synthalen M was dispersed in water, then tiethanolamine, preservative, propylene glycole and ethanol mixture, wherein the compound of Example 1 was previously dissolved, was added, perfume was last added.

EXAMPLE 10

1000 g of low density polyethylene (Riblene EF 2100 R Enichem), 2 g of n-octadecyl-3-(3,5-di-terbutyl-4-hydroxyphenyl) propionate, 1 g of calcium stearate and 0.3 g of a compound of formula (I) were homogeneously mixed. The obtained mixtures were extruded at 190° C. and transformed into granules. From these, by pressing at 200° C., films of 0,2 mm were obtained.

Samples of these films were subjected to UV radiations in a Weatheromether WOM Ci-65 at a black panel temperature of 63° C. The T-0.1 time necessary to increase the carbonylic band at 5.85 nm of 0.1 compared with films containing no stabilizer, was determined in the irradiated samples. The results are reported in Table 2.

TABLE 2

| Stabilizing agent | T 0.1 (Hours) |
| --- | --- |
| No agent | 340 |
| Compound of Example 1 | 1270 |
| Compound of Example 2 | 1080 |
| Compound of Example 4 | 1160 |

I claim:

1. A compound of formula (I)

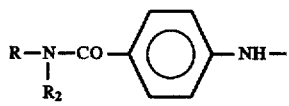 (I)

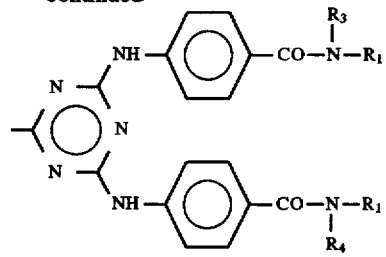

wherein R and $R_1$ can be the same or different and are $C_1$–$C_{18}$ straight or branched alkyl, $C_5$–$C_{12}$ cycloalkyl optionally substituted with one or more $C_1$–$C_4$ alkyl; $R_2$, $R_3$ and $R_4$ can be the same or different and have the same meaning of R or are hydrogen.

2. A compound according to claim 1, wherein R and $R_1$ have the above defined meaning, $R_2$ is hydrogen, $R_3$ and $R_4$ have the same meaning of R and $R_1$, or are hydrogen.

3. A compound according to claim 1, wherein $R_2$, $R_3$ and $R_4$ are hydrogen, R and $R_1$ have the above defined meaning.

* * * * *